United States Patent [19]

Iida et al.

[11] Patent Number: 5,792,842
[45] Date of Patent: Aug. 11, 1998

[54] GANGLIOSIDE GM3 DERIVATIVE HAVING FLUORINE ATOM AT 9-POSITION OF SIALIC ACID AND INTERMEDIATES THEREFOR

[75] Inventors: Takao Iida; Yutaka Ohira, both of Ibaraki, Japan

[73] Assignee: Daikin Industries Ltd., Osaka, Japan

[21] Appl. No.: 624,604

[22] PCT Filed: Aug. 10, 1995

[86] PCT No.: PCT/JP95/01598

§ 371 Date: Apr. 16, 1996

§ 102(e) Date: Apr. 16, 1996

[87] PCT Pub. No.: WO96/05211

PCT Pub. Date: Feb. 22, 1996

[30] Foreign Application Priority Data

Aug. 16, 1994 [JP] Japan ................... 6-192486

[51] Int. Cl.$^6$ .............. A61K 31/70; C08B 3/02; C08B 3/04; C08B 5/04
[52] U.S. Cl. .............. 536/17.2; 514/23; 514/24; 514/25; 514/53; 514/54; 514/61; 536/18.7; 536/53; 536/54; 536/55.3; 536/120; 536/122; 536/123; 536/123.1; 536/123.13
[58] Field of Search .............. 536/53, 54, 55.3, 536/123, 123.1, 123.13, 17.2, 18.7, 120, 122, 4.1; 514/53, 54, 61, 23, 24, 25

[56] References Cited

U.S. PATENT DOCUMENTS

| | | | |
|---|---|---|---|
| 4,918,170 | 4/1990 | Hasegawa et al. | 536/1.1 |
| 5,559,103 | 9/1996 | Gaeta et al. | 514/54 |
| 5,583,208 | 12/1996 | Iida et al. | 536/17.9 |

FOREIGN PATENT DOCUMENTS

WO91/10744  7/1991  WIPO.

OTHER PUBLICATIONS

Liu et al., *J. Amer. Chem. Soc.*, vol. 114(10): 3901–3910, (1992). (Abstract Only).

Selected Lecture Notes from 3rd European Training Course on Carbohydrates 1994 (Jun. 26–Jul. 1, 1994), Monastery Rolduc, Kerkrade—The Netherlands (Abstract Only).

Suzuki, "Seita No Kagaku" (Science of Living Bodies), 38 (4), pp. 332–339 (1987).

Suzuki, Biochemistry, 62 (4), pp. 231–260 (1990).

Suzuki et al, Glycoconjugate J. vol. 7, pp. 346–356 (1990).

Sharma et al, Carbohydrate Research, vol. 175, No. 1, pp. 25–34 (1988).

Petrie III et al, Carbohydrate Research, vol. 186, No. 2, pp. 326–334 (1989).

*Primary Examiner*—John Kight
*Assistant Examiner*—Howard C. Lee
*Attorney, Agent, or Firm*—Birch, Stewart, Kolasch & Birch, LLP

[57] ABSTRACT

A ganglioside GM3 derivative having a fluorine atom at the 9-position of sialic acid represented by the formula:

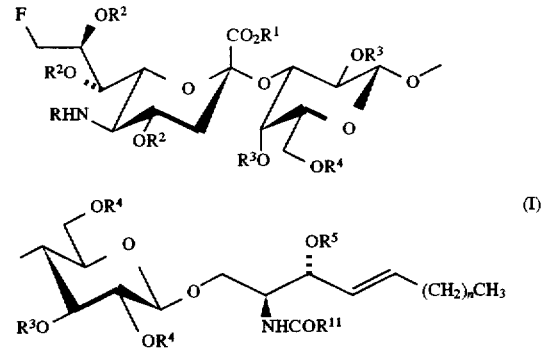

wherein R is an aliphatic lower acyl group, $R^1$ is a hydrogen atom or a lower alkyl group, $R^2$ to $R^5$ represent independently of one another a hydrogen atom, an aliphatic lower acyl group or an aromatic acyl group, $R^{11}$ is an straight or branched, saturated or unsaturated aliphatic hydrocarbon group having 1 to 30 carbon atoms, and n is an integer of 0 to 20, provided that when $R^1$ is a hydrogen atom, $R^2$ to $R^5$ are hydrogen atoms, or when $R^1$ is a lower alkyl group, $R^2$ to $R^5$ are each an aliphatic lower acyl group or an aromatic acyl group, and intermediates therefor. This compound is useful as an agent for preventing infection of the influenza virus, an agent for preventing proliferation and metastasis of the cancer cells, etc.

6 Claims, No Drawings

GANGLIOSIDE GM3 DERIVATIVE HAVING FLUORINE ATOM AT 9-POSITION OF SIALIC ACID AND INTERMEDIATES THEREFOR

FIELD OF THE INVENTION

The present invention relates to a ganglioside GM3 derivative in which a hydroxyl group at the C-9 position of sialic acid is replaced by a fluorine atom and which contributes to various biological phenomena as a biologically active glycolipid, and intermediates therefor.

DESCRIPTION OF THE PRIOR ART

Ganglioside is a collective name of sphingoglucolipids having a sialic acid group, and an amphipathic molecule comprising a hydrophilic saccharide chain and a hydrophobic ceramide moiety. Depending on their structures, in particular, kinds of the saccharide structures, they have abbreviations such as GM1, GM2, GM3, GM4, GD2, GD3, GT2, GT3, GT1b, and so on, and they are localized in various tissues as minor components in biomembranes.

In these years, the gangliosides attract attentions, as they are revealed to play a fundamental role as receptor molecules for various cytotoxins, hormones, interferons, neurotransmitters, and influenza viruses (Y. Suzuki, "SEITAI NO KAGAKU" (Science of Living Bodies), 38 (4), 332–339 (1987)). For example, on a cell surface of the influenza virus, hemaglutinine and sialitase which identify the saccharide chain containing sialic acid are present, and they play an important role in absorption and penetration of the influenza virus in mammal cells. When mechanisms of the absorption and penetration of the influenza virus are viewed from the host side, they are important components to prevent infections of the virus (Y. Suzuki, Biochemistry, 62 (4), 231–260 (1990)).

From the above view point, Suzuki et al studied the influence of various ganglioside derivatives on the activity of influenzaneuraminidase, and obtained interesting results (Suzuki et al, Glycoconjugate J., 7 (1990)).

Such compound that is bound with the virusneuraminidase strongly but does not act as a substrate is extremely useful in the analysis of a three-dimensional active center structure of this enzyme, and also expected to open a new way for preventing virus infection.

The sialic acid moiety which is partially acetylated in the ganglioside is protected against the function of sialidase, and assumed to be a factor which will cause a carcinomatous change on antigenicity of human melanoma and a change on the antigenicity of cytopolysaccharide. Further, the partially acetylated sialic acid residue may have an important function in the bonding of the ganglioside with the virus.

Sialic acid is a collective name of a group of neuramic acid derivatives, and has acetyl or glycolyl groups as substituents of amino acids, and an acetyl, lactyl, phosphate ester, sulfate ester or methyl group as a substituent of a hydroxyl group. Today, 30 sialic acids are found, and their chemical structures have been determined.

In addition, it is found that the ganglioside takes part in the mechanisms of proliferation and metastasis of cancer cells. That is, the natural ganglioside GM3 has a property to suppress the proliferation of cells, and it is desired to selectively exercise this function on the cancer cells. Since the adhesion of the cancer cells to endothelial cells in blood vessels and exudation of the cancer cells outside the blood vessels are caused by the function of the ganglioside in the cancer metastasis, it is desired to provide a medical agent which prevents the metastasis.

The major functions of the sialic acid are 1) charging negative charge to complex carbohydrates, and cell membranes; 2) influence on a conformation of the glycolipids and glycoproteins; 3) information transfer; 4) masking of antigen sites; and so on, and increasing interest will be given to the functions of sialic acid.

As explained above, the gangliosides take part in various life phenomena as the functional molecule. Among the constitutive components of the ganglioside, sialic acid is assumed to have a large influence on the expression of activities thereof.

As seen from the above descriptions, sialic acid is one of the important constitutive components of the ganglioside which contributes to the various life phenomena. Then, it will be necessary to synthesize various gangliosides comprising organic chemically modified sialic acid in order to study the influence of the structure of sialic acid on the expression of the activities thereof, and it is desired to clarify the functions of the gangliosides in the molecule level using the synthesized compounds.

SUMMARY OF THE INVENTION

An object of the present invention is to provide a ganglioside GM3 derivative which is useful as an agent for preventing infection of the influenza virus, an agent for preventing proliferation and metastasis of the cancer cells, etc.

Another object of the present invention is to provide an intermediate which is useful in the preparation of such ganglioside GM3 derivative.

According to a first aspect of the present invention, there is provided a ganglioside GM3 derivative having a fluorine atom at the 9-position of sialic acid represented by the formula (I):

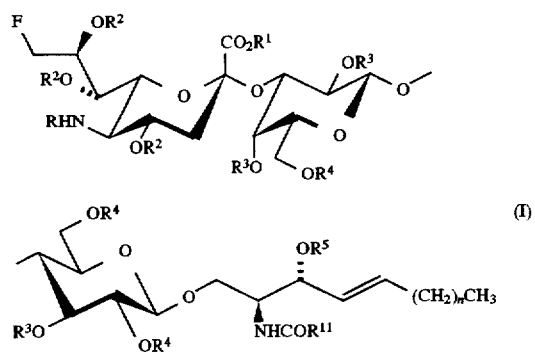

wherein R is an aliphatic lower acyl group, $R^1$ is a hydrogen atom or a lower alkyl group, $R^2$ to $R^5$ represent independently of one another a hydrogen atom, an aliphatic lower acyl group or an aromatic acyl group, $R^{11}$ is an straight or branched, saturated or unsaturated aliphatic hydrocarbon group having 1 to 30 carbon atoms, and n is an integer of 0 to 20, provided that when $R^1$ is a hydrogen atom, $R^2$ to $R^5$ are hydrogen atoms, or when $R^1$ is a lower alkyl group, $R^2$ to $R^5$ are each an aliphatic lower acyl group or an aromatic acyl group.

According to a second aspect of the present invention, there is provided an intermediate of the compound of the above formula (I), which is represented by the formula (II):

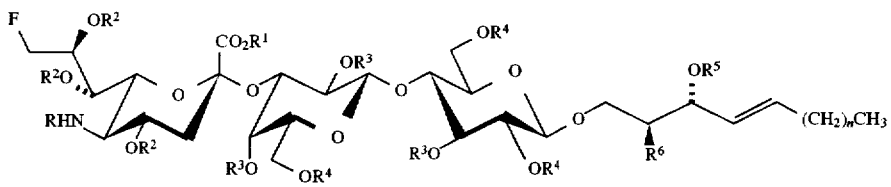
(II)

wherein $R^6$ is a $N_3$ group or a $NH_2$ group, R, $R^1$, $R^2$ to $R^5$ and n are the same as defined above, provided that when $R^1$ is a hydrogen atom, $R^2$ to $R^5$ are hydrogen atoms, or when $R^1$ is a lower alkyl group, $R^2$ to $R^5$ are each an aliphatic lower acyl group or an aromatic acyl group.

According to a third aspect of the present invention, there is provided an intermediate of the compound of the above formula (II), which is represented by the formula:

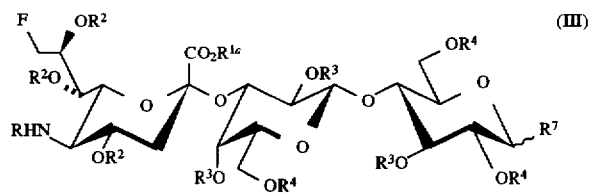
(III)

wherein $R^{1a}$ is a lower alkyl group, $R^7$ is a hydroxyl group, a fluorine atom or a —OC(=NH)CCl$_3$ group, R, $R^2$, $R^3$ and $R^4$ are the same as defined above, provided that when $R^7$ is a fluorine atom or a —OC(=NH)CCl$_3$ group, $R^2$, $R^3$ and $R^4$ are each an aliphatic lower acyl group or an aromatic acyl group.

According to a fourth aspect of the present invention, there is provided an intermediate of the compound of the above formula (III), which is represented by the formula (IV):

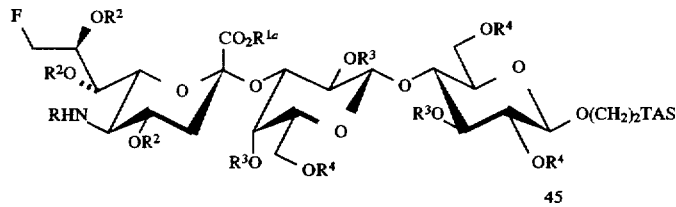
(IV)

wherein TAS represents a trialkylsilyl group, and R, $R^{1a}$ and $R^2$ to $R^4$ are the same as defined above.

According to a fifth aspect of the present invention, there is provided an intermediate of the compound of the above formula (IV), which is represented by the formula (V):

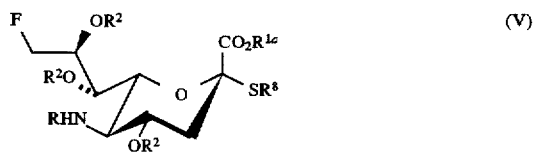
(V)

wherein $R^8$ is a lower alkyl group or an aliphatic acyl group, and R, $R^{1a}$ and $R^2$ are the same as defined above.

According to a sixth aspect of the present invention, there is provided an intermediate of the compound of the above formula (V), which is represented by the formula (VI):

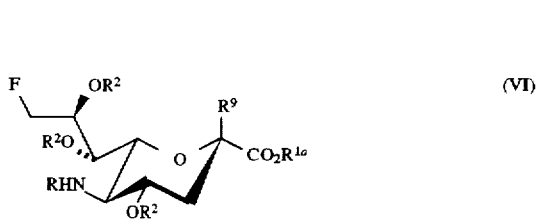
(VI)

wherein $R^9$ is a hydroxyl group or a halogen atom, and R, $R^{1a}$ and $R^2$ are the same as defined above.

DETAILED DESCRIPTION OF THE INVENTION

Herein, the lower alkyl group means an alkyl group having 1 to 4 carbon atoms. The aliphatic lower acyl group means an aliphatic acyl group having 1 to 4 carbon atoms, and the aromatic acyl group means an aromatic acyl group having 6 to 8 carbon atoms. In the trialkylsilyl group, an alkyl group has 1 to 4 carbon atoms.

As understood from the above chemical structure, the fluorine-substituted ganglioside GM3 derivative of the present invention consists of a sialic acid derivative moiety, a lactose moiety, and a ceramide moiety, and is a derivative in which the hydroxyl group at the 9-position of the sialic acid is replaced by the fluorine atom. This ganglioside GM3 derivative can be prepared by reaction steps comprising first synthesizing a thioalkyl compound of the fluorine-containing sialic acid derivative, condensing this thioalkyl compound with a 2,6,6'-triacyl derivative of lactose to obtain a sialyllactose derivative, and then introducing a ceramide moiety. Hereinafter, the preparation method of the fluorine-substituted ganglioside GM3 derivative of the present invention will be explained.

As a starting compound in the preparation of the fluorine-substituted ganglioside GM3 derivative (I) of the present invention, for example, 9-deoxy-9-fluoro-N-acetyl-neuraminic acid is used. This compound is easily synthesized according to the process described in, for example, Carbohydrate Research, 175 (1988) 25–34. That is, benzyl-2-acetamide-2-deoxy-Δ-D-glucopyranoide (available from Sigma) as a starting compound is subjected to 1) 6-O-tritylation, 2) 3,4-di-O-benzylation, and 3) detritylation at the 6-position, followed by 4) a reaction with diethylaminosulfur trifluoride to obtain benzyl-2-acetamide-2,6-dideoxy-3,4-di-O-benzyl-Δ-D-glucopyranoide. Then, this compound is debenzylated with hydrogen using a palladium/carbon catalyst to obtain 2-acetamide-2,6-dideoxy-6-fluoro-O-glucose. This glucose derivative is isomerized in water at pH 11, whereby about 20% is converted to acetamide-2,6-dideoxy-6-fluoromannose.

The obtained mixture is converted to 9-deoxy-9-fluoro-N-acetyl-neuraminic acid by the action of N-acetylneuraminic acid aldolase, and isolated by an ion exchange resin.

By esterifying a carboxylic acid moiety at the 1-position of the above obtained compound with an alcohol, a compound of the formula:

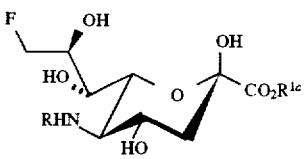
(VI-1)

wherein R is an aliphatic lower acyl group, and $R^{1a}$ is a lower alkyl group is obtained.

The esterification is performed as follows:

For example, in the case of a methyl ester, a cation exchange resin (H+ type) which is dried overnight in a vacuum desiccator containing diphosphorus pentoxide and the above starting compound are charged in anhydrous methanol, and reacted at room temperature for 1 to 6 hours, preferably 2 to 3 hours, followed by the removal of the ion exchange resin by filtration and concentration to obtain an esterified compound.

Then, the compound of the above formula (VI-1) is reacted with an acyl halide of the formula:

$R^{2a}X$ wherein $R^{2a}$ is an aliphatic lower acyl group or an aromatic acyl group, and X is a halogen atom, for example, acetyl chloride, to acylate the hydroxyl groups at the 4, 7 and 8-positions and replace the OH group at the 2-position by a halogen atom, to obtain a compound of the formula:

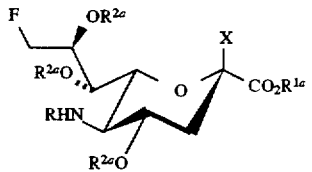
(VI-2)

wherein $R^{2a}$ is an aliphatic lower acyl group or an aromatic acyl group, X is a halogen atom, and R and $R^{1a}$ are the same as defined above.

Then, to the compound of the above formula (VI-2) which is dissolved in anhydrous dichloromethane, thioacetic acid and then potassium thioacetate are added while cooling with ice, and reacted at room temperature to thioacetylate the halogen atom at the 2-position, to obtain a compound of the formula:

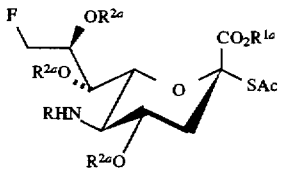
(VII)

wherein Ac represents an acetyl group, and R, $R^{1a}$ and $R^{2a}$ are the same as defined above.

The compound of the formula (VII) is reacted with an alkali metal alkoxide such as sodium methoxide in an alcoholic solvent at a low temperature, followed by the removal of the solvent to obtain a compound of the formula:

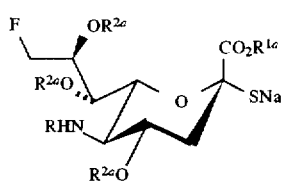
(VIII)

wherein R, $R^{1a}$ and $R^{2a}$ are the same as defined above. This compound (VIII) is then reacted with an alkyl iodide such as methyl iodide in a suitable aprotic solvent such as dimethylformamide at room temperature or a slightly elevated temperature, followed by post-treatment by a conventional method to obtain a thioalkyl compound of the sialic acid derivative of the formula:

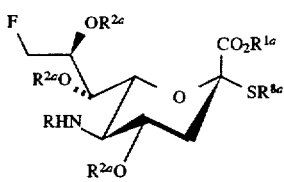
(V-1)

wherein $R^{8a}$ is a lower alkyl group, and R, $R^{1a}$ and $R^{2a}$ are the same as defined above.

Then, the above prepared thioalkyl compound of the sialic acid derivative is condensed with the 2,6,6'-triacyl compound of lactose of the formula:

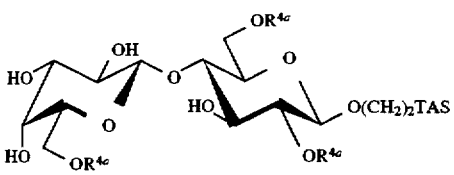
(IX)

wherein $R^{4a}$ is an aliphatic lower acyl group or an aromatic acyl group, and TAS represents a trialkylsilyl group.

The compound of the formula (IX) can be easily synthesized according to the process disclosed in JP-A-3-101691. That is, first, 2-(trialkylsilyl)ethyl-β-D-lactone is benzylated only at the 3'-position with di-n-butyltin oxide, tetra-n-butylammonium bromide and benzyl bromide in a nonpolar solvent (e.g. benzene, toluene, chloroform, dichloromethane, etc.), and treated with an acylating agent (e.g. benzoyl chloride, etc.) in the presence of a base such as pyridine while cooling if desired, according to a general method of acylation to selectively acylate the 2-, 6- and 6'-positions, followed by elimination of the benzyl group at the 3'-position only, to obtain the compound of the formula (IX).

In the condensation reaction, the thioalkyl compound of the sialic acid of the formula (V-1) and the 2,6,6'-triacyl compound of lactose of the formula (IX) are dissolved in a solvent such as anhydrous propionitrile, activated molecular sieve 4A is added to the solution, and the mixture is stirred overnight under nitrogen atmosphere. Thereafter, the mixture is cooled to a low temperature, and N-iodosuccinimide and then trifluoromethanesulfonic acid are added and reacted at −45° to −40° C. When a condensation promotor such as N-iodosuccinimide and a catalytic amount of trifluoromethanesulfonic acid are used in the propionitrile solvent, a sialyllactose derivative of the formula:

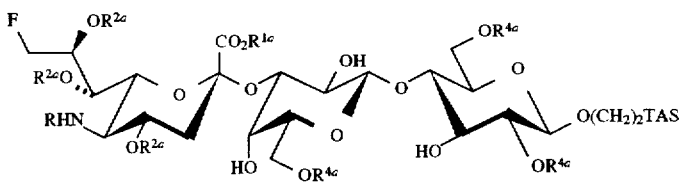

(IV-1)

wherein R, $R^{1a}$, $R^{2a}$, $R^{4a}$ and TAS are the same as defined above is obtained regioselectively and stereoselectively.

The free hydroxyl groups of the obtained sialyl lactose derivative are acylated and protected to obtain a compound of the formula (IV-2):

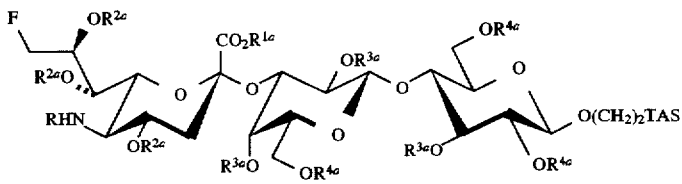

(IV-2)

wherein R3a is an aliphatic lower acyl group or an aromatic acyl group, and R, $R^{1a}$, $R^{2a}$, $R^{4a}$ and TAS are the same as defined above.

The acylation can be performed by dissolving the compound of the formula (IV-1) in a solvent, for example, pyridine and reacting the compound with an acyl halide or an acid anhydride at room temperature.

Then, boron trifluoride-ether is reacted with the compound of the formula (IV-2) to eliminate the $(CH_2)_2TAS$ group at the 2-position to obtain a compound of the formula (III-1):

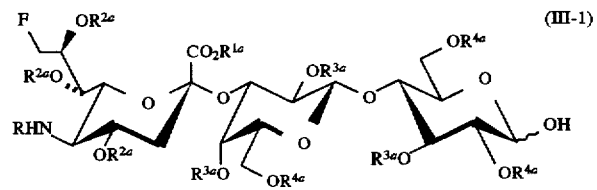

(III-1)

wherein R and $R^{1a}$ to $R^{4a}$ are the same as defined above.

The elimination of the $(CH_2)_2TAS$ group is performed by dissolving the compound of the formula (IV-2) in dichloromethane, dropwise adding boron trifluoride-diethyl ether to the solution while cooling with ice and reacting them at room temperature under argon atmosphere.

Then, to activate the OH group in the glucose moiety of the compound of the formula (III-1), it is changed to a —OC(=NH)CCl₃ group or a fluorine atom.

To obtain a trichloroacetoimidate compound, for example, the compound of the formula (III-1) is dissolved in dichloromethane under argon atmosphere, and trichloroacetonitrile and 1,8-diazabicyclo[5.4.0]undec-7-ene are added to the solution which is cooled at −5° C., and reacted while cooling with ice.

To obtain a fluorinated compound, the compound of the formula (III-1) is reacted with diethylaminosulfato trifluoride are reacted in dichloromethane at a temperature of −10° to 30° C., preferably 0° to 10° C.

By the above steps, a compound of the formula (III-2):

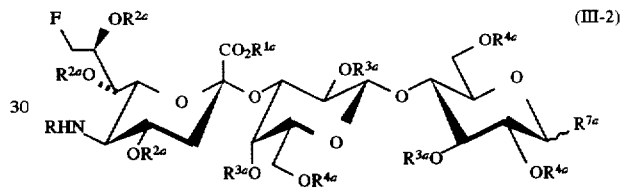

(III-2)

wherein $R^{7a}$ is a —OC(=NH)CCl₃ group or a fluorine atom, and R and $R^{1a}$ to $R^{4a}$ are the same as defined above.

Next, the compound of the formula (III-2) is condensed with a azidOsphingosine derivative of the formula (X):

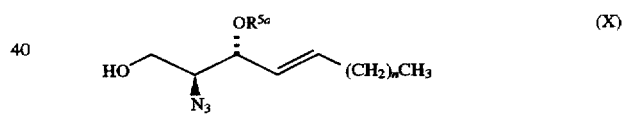

(X)

wherein $R^5$ is an aliphatic lower acyl group or an aromatic acyl group, and n is an integer of 0 to 20.

The azidosphingosine derivative may be easily obtained according to the method described in Carbohydrate Research, 202 (1990) 177–191, by synthesizing azidosphingosine, protecting a primary hydroxyl group at the 1-position with a suitable protecting group such as a triphenylmethyl group, protecting a hydroxyl group at the 3-position with an acyl chloride such as benzoyl chloride by a conventional method, and then eliminating the protecting group at the 1-position with, for example, boron trifluoride-diethyl ether.

When $R^{7a}$ is the —OC(=NH)CCl₃ group, the condensation reaction can be performed by dissolving the compound of the formula (III-2) and the compound of the formula (X) in dichloromethane, adding activated powdery molecular sieve 4A to the solution, stirring the mixture for 30 minutes under argon atmosphere, dropwise adding boron trifluoride-diethyl ether while cooling with ice, and reacting them at 0° C.

When $R^{7a}$ is a fluorine atom, the condensation reaction can be performed by reacting the compound of the formula (III-2) and the compound of the formula (X) in dichloromethane in the presence of stannous chloride and silver perchlorate at a temperature of 15° to 25° C.

Accordingly, a compound of the formula (II-1):

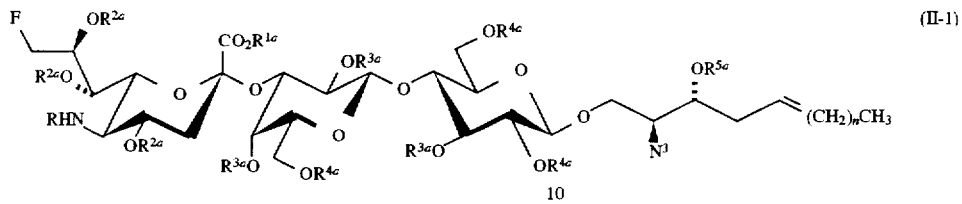

wherein R, $R^{1a}$ to $R^{5a}$ and n are the same as defined above is obtained.

Then, an azido group of this compound is reduced to an amino group in a tributylphosphine or triphenylphosphine/water system or a hydrogen sulfide/pyridine system to obtain a compound of the formula (II-2):

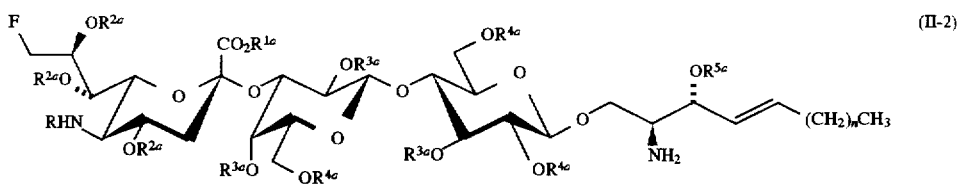

wherein R, $R^{1a}$ to $R^{5a}$ and n are the same as defined above is obtained.

The amino group of the above compound and a carboxyl group of a compound of the formula (XI):

wherein $R^{11}$ is a straight or branched, saturated or unsaturated aliphatic hydrocarbon group having 1 to 30 carbon atoms are condensed to form an amide bond using a dehydrating agent such as dicyclohexylcarbodiimde (DCC), diisopropylcarbodiimide (DIPC), N-ethyl-N'-3-dimethylaminopropylcarbodiimide (WSCI), etc., whereby 25 a compound of the formula (I-1):

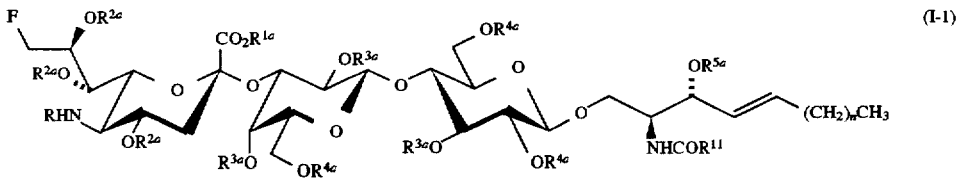

wherein R, $R^{1a}$ to $R^{5a}$, $R^{11}$ and n are the same as defined above is obtained.

In this reaction, a molar ratio of the compound of the formula (II-2) to the compound of the formula (XI) is from 1:05 to 1:2.0, preferably from 1:1 to 1:1.1. The dehydrating agent is used in an amount of 1 to 2 moles, preferably 1 to 1.1 moles per one mole of the compound of the formula (II-2). Preferred examples of the solvent are dichloromethane, chloroform, dichloroethane, dimethylformamide, and so on. A reaction temperature is usually from 15 to 25° C. After the completion of the reaction, the reaction mixture is subjected to post-treatment such as extraction, evaporation off of the solvent, etc., and the product is purified by column chromatography, if desired.

From the obtained compound of the formula (I-1), the protecting groups of the hydroxyl group and the carboxyl group are eliminated to obtain the ganglioside GM3 derivative of the present invention in which the hydroxyl group at the 9-position of the sialic acid is replaced by the fluorine atom and which is represented by the formula (I-2):

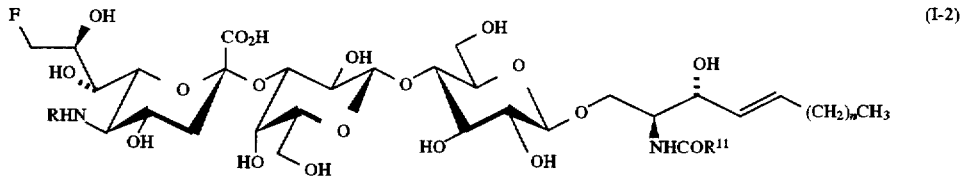

wherein R, $R^{11}$ and n are the same as defined above.

For example, this reaction may be performed as follows:
The compound of the formula (I -1) is dissolved in anhydrous methanol, and 2 to 4 times equivalents of sodium methoxide is added to the solution, and reacted at a temperature from room temperature to 50° C. for 30 minutes to 10 hours to eliminate the protecting group of the hydroxyl group. Then, after the mixture is cooled to 0° C., water is added to the mixture and stirred at the same temperature for 1 to 6 hours to eliminate the protecting group of the carboxyl group. After desalting with a H+ type cation exchange resin, the mixture is column purified using Sephadex LH-20 to obtain the ganglioside GM3 derivative in which the hydroxyl group at the 9-position of the sialic acid is replaced by the fluorine atom and which is represented by the formula (I-2).

The protecting groups of the hydroxyl group and the carboxyl group can be eliminated from the compounds of the formulas (IV-1), (IV-2), (III-1), (III-2), (II-1) and (II-2) under the same conditions as above.

As explained above, sialic acid is one of the important constitutive components of the ganglioside which contributes to the various life phenomena. Then, it is useful to synthesize the gangliosides which are organic chemically modified with the fluorine atom in order to study the influence of the structure of sialic acid on the expression of the activities thereof.

The fluorine-substituted gangliosides of the present invention have some functions relating to biological activities such as large resistance to neuraminidase, and protected from metabolic decomposition, as well as recognition of cells. In addition, they are useful in development and clinical application of practical medicines such as an agent for preventing infection, an agent for preventing proliferation and metastasis of cancer cells, an agent for preventing bonding of leukocytes or cancer cells to a blood vessel wall, so on.

EXAMPLES

The present invention will be illustrated by the Examples, which do not limit the scope of the present invention.

The ganglioside derivative the 9-position of which is replaced by the fluorine atom was synthesized according to the following reaction scheme:

Reaction Scheme 1

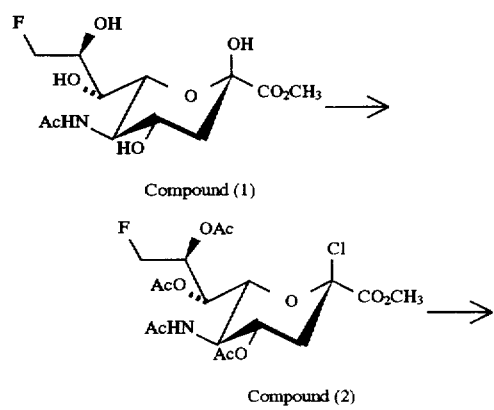

Compound (1)

Compound (2)

-continued
Reaction Scheme 1

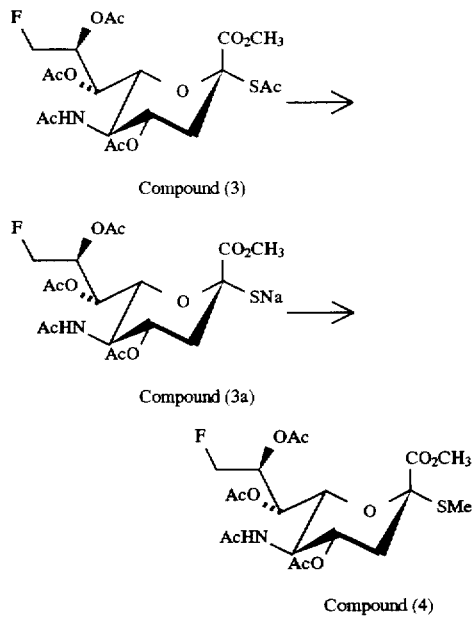

Compound (3)

Compound (3a)

Compound (4)

Example 1
Synthesis of methyl (5-acetamide-3,5,9-trideoxy-9-fluoro-D-glycero-β-D-galacto-2-nonulopyranoside)nate (Compound (1))

9-Deoxy-9-fluoro-N-acetylneuraminic acid (1.09 g, 3.5 mmol) was dissolved in anhydrous methanol (100 ml). To the solution, Dowex 50W-X8 (6.2 g) was added, and the mixture was stirred at room temperature (22° C.) for 2.5 hours under argon atmosphere. After separating the solution by decantation, an insoluble material was washed with methanol (50 ml×3), and a methanol-soluble material was combined with the solution and concentrated under reduced pressure. The residue was recrystallized from methanol-ethyl acetate to obtain the Compound (1) (0.71 g). Yield, 62.5%.

Melting point: 128–131.5° C. $C_{12}H_{20}NO_8F$ (325.30) $[\alpha]_D=+21.0°$ (c 0.20, $CHCl_3$) $IR^{KBr}_{max}cm^{-1}$: 3700–3150 (OH, NH), 1750 (ester), 1650, 1540 (amide). $^1H$-NMR ($D_2O$; TSP): δ 1.93 (1H, dd, $J_{3a,4}=11.7$ Hz, $J_{3a,3e}=11.8$ Hz, H-3a), 2.33 (1H, dd, $J_{3e,4}=4.9$ Hz, $J_{3a,3e}=13.2$ Hz, H-3e), 3.85 (3H, s, $CO_2Me$). 19F-NMR ($D_2O$; $CFCl_3$): δ -208 (dt, $J_{F,9H}=50.5$ Hz, $J_{F,8H}=29.5$ Hz, 1F, 9-F)

Example 2
Synthesis of methyl (5-acetamide-4,7,8-tri-O-acetyl-2-chloro-3,5,9-trideoxy-9-fluoro-D-glycero-β-D-galacto-2-nonulopyraside)nate (Compound (2))

The compound (1) (3.40 g, 10.5 mmol) was added to acetyl chloride (100 ml) and stirred at 38° C. for 22.5 hours. After confirming the termination of the reaction by TLC (chloroform acetone=7:3), the reaction mixture was concentrated at a temperature of 30° C. or lower under reduced pressure, and the residue was dissolved in anhydrous benzene, followed by concentration under reduced pressure to obtain the crude compound (2) (4.80 g). Yield, 97.7%.

$C_{18}H_{25}NO_{10}ClF$ (469.86) $IR^{KBr}_{max}cm-1$: 3700–3150 (NH), 1750 (ester), 1650, 1540 (amide). $^1H$-NMR ($CDCl_3$; TMS): δ 1.92–2.14 (12H, s, 3OAc, NHAc), 2.79 (1H, dd, $J_{3e,4}=4.8$ Hz, $J_{3a,3e}=13.9$ Hz, H-3e), 3.89 (3H, s, $CO_2Me$). $^{19}F$-NMR ($CDCl_3$; $CFCl_3$): δ -234 (dt, $J_{F,9H}=50.0$ Hz, $J_{F,8H}=24.5$ Hz, 1F, 9-F).

Example 3
Synthesis of methyl (5-acetamide-4,7,8-tri-O-acetyl-2-S-acetyl-3,5,9-trideoxy-9-fluoro-2-thio-D-glycero-a-D-galacto-2-nonulopyraside)nate (Compound (3))

The Compound (2) (338 mg, 0.72 mmol) was dissolved in anhydrous dichloromethane (3 ml). To the solution, thioacetic acid (4 μl, 0.06 mmol) and then potassium thioacetate (357 mg, 3.13 mmol) were added, and stirred at room temperature for 21 hours. After confirming the termination of the reaction by TLC (chloroform:ethyl acetate=1:1), the reaction mixture was concentrated, and the residue was dissolved in chloroform and washed with water, followed by drying over magnesium sulfate. The mixture was filtrated and washed with chloroform. The filtrate and the washing liquid were combined, and concentrated under reduced pressure. The residue was subjected to flash chromatography (eluent, chloroform ethyl acetate=1:1) to obtain the Compound (3) (240 mg). Yield, 65.4%.

$C_{20}H_{28}NO_{11}FS$ (509.52) $^1$H-NMR (CDCl$_3$; TMS): δ 1.88 (s, 3H, NAc), 1.94 (dd, 1H, $J_{3a,3e}=J_{3a,4}$=12.8 Hz, H-3a), 2.02, 2.14, 2.17, 2.29 (4s, 12H, 3OAc, SAc), 2.67 (1H, dd,$J_{3e,4}$=4.6 Hz, $J_{3a,3e}$=13.0 Hz, H-3e), 3.80 (3H, s, CO$_2$Me), 4.59 (dd, $^1$H, $J_{5,6}$=10.8 Hz, $J_{6,7}$=2.3 Hz, H-6), 4.94 (ddd, 1H, $J_{3e,4}$=4.6 Hz, $J_{4,5}$=10.5 Hz, $J_{3a,4}$=11.6 Hz, H-4), 5.15 (m, 1H, H-8), 5.48 (d, 1H, $J_{5,NH}$32 8.9 Hz, NH), $_{19}$F-NMR (CDCl$_3$; CFCl$_3$): δ -234 (dt, $J_{F,9H}$=50.5 Hz, $J_{F,8H}$=24.5 Hz, 1F, 9-F).

Example 4
Synthesis of methyl (methyl 5-acetamide-4,7,8-tri-O-acetyl-3,5,9-trideoxy-9-fluoro-2-thio-D-glycero-α-D-galacto-2-nonulopyraside)nate (Compound (4))

The compound (3) (1.01 g, 1.98 mmol) was dissolved in anhydrous methanol (25 ml), and to the solution, a solution of metal sodium (34.6 mg, 1.51 mmol) dissolved in methanol (10 ml) was dropwise added and stirred for 7 minutes. Thereafter, the solution was concentrated in vacuo while cooling with iced water, and thoroughly dried. Then, the residue was dissolved in anhydrous dimethylformamide (8 ml). To the solution, methyl iodide (0.30 ml, 4.8 mmol) was added and stirred at room temperature for 17 hours. The residue obtained by concentration under reduced pressure was subjected to column chromatography (eluent, dichloromethane: methanol=100:1→90:1) to obtain the Compound (4) (695 mg).

Yield, 72.9%. $C_{19}H_{28}NO_{10}FS$ (481.51) $|α|_D$=+36.5° (c 0.38, CHCl$_3$) IR$^{KBr}_{max}$cm$^{31}$ $^1$: 3700–3150, 3150–2800, 1750, 1650, 1540. $^1$H-NMR (CDCl$_3$; TMS: δ 1.88 (s, 3H, NAc), 1.99 (dd, 1H, $J_{3a,3e}=J_{3a,4}$=12.1 Hz, H-3a), 2.03, 2.12, 2.16, 2.19 (4s, 12H, 3OAc, SAc), 2.74 (1H, dd, $J_{3e,4}$=4.7 Hz, $J_{3a,3e}$=12.7 Hz, H-3e), 3.84 (dd, 1H, $J_{5,6}$=10.7 Hz, $J_{6,7}$=2.0 Hz, H-6), 3.82 (3H, s, CO$_2$Me), 4.12 (ddd, 1H, $J_{4,5}=J_{5,6}$=$J_{5,NH}$=10.5 Hz, H-5), 4.90 (ddd, 1H, $J_{3e,4}$=4.6 Hz, $J_{4,5}$=10.4 Hz, $J_{3a,4}$=11.6 Hz, H-4), 5.3–5.4 (m, 2H, H-7, H-8), 5.13 (d, 1H, $J_{5,NH}$=10.2 Hz, NH). $^{19}$F-NMR (CDCl$_3$; CFCl$_3$): δ -235 (dt, $J_{F,9H}$=50.0 Hz, $J_{F,8H}$=23.5 Hz, 1F, 9-F).

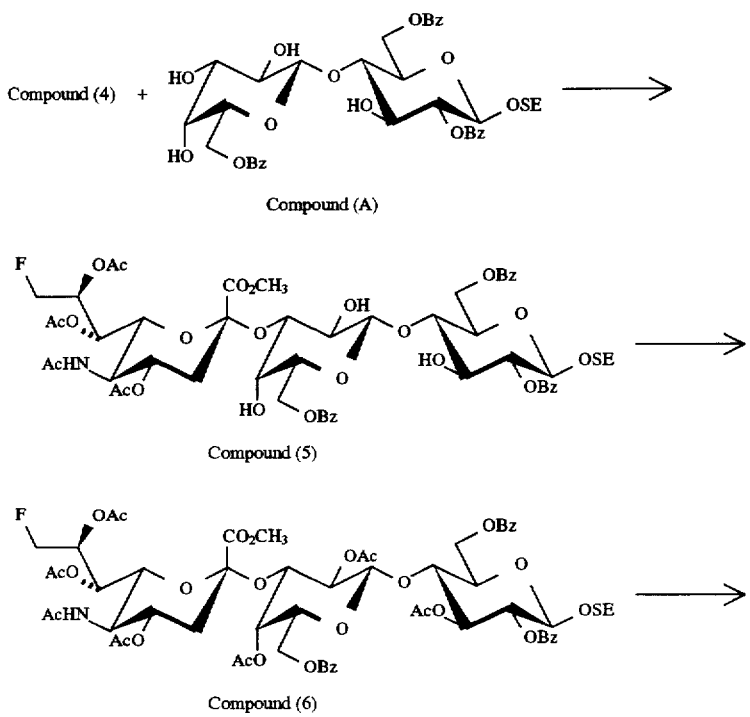

Reaction Scheme 2

-continued
Reaction Scheme 2

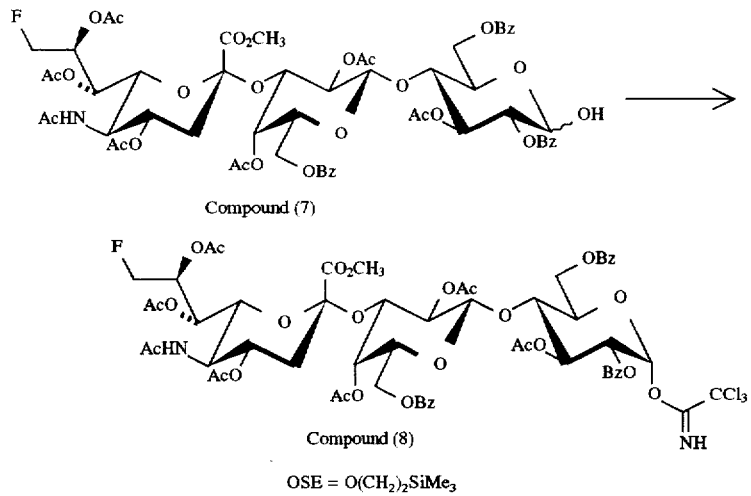

Compound (7)

Compound (8)

OSE = O(CH$_2$)$_2$SiMe$_3$

Example 5
Synthesis of 2-(trimethylsilyl)ethyl O-(methyl 5-acetamide-4,7,8-tri-O-acetyl-3,5,9-trideoxy-9-fluoro-D-glycero-α-D-galacto-2-nonulopyrasilonate)-(2→3)-O-(6-O-benzoyl-β-D-galactopyranosil)-(1→4)-2,6-di-O-benzoyl-β-D-glucopyranoside (Compound (5))

The compound (4) (846 mg, 1.76 mmol) and 2-(trimethylsilyl)ethyl O-(6-O-benzoyl-β-D-galactopyranosil)-(1→4)-2,6-di-O-benzoyl-β-D-glucopyranoside (Compound (A)) (614 mg, 0.81 mmol) were dissolved in anhydrous propionitrile (8 ml). To the solution, molecular sieve 4A (3 g), which was activated by drying at 180° C. for 6 hours in vacuo, was added and stirred overnight under argon atmosphere. After cooling to −45° C., N-iodosuccinimide (1.08 g, 4.80 mmol), and then trifluoromethanesulfonic acid (24 μl, 0.27 mmol) were added to the mixture, and stirred at −45° to −40° C. for 2 hours. The reaction mixture was diluted with chloroform and filtrated through sellaite, and undissolved materials were washed with chloroform. The filtrate and the washing liquid were combined, and the organic layer was washed with a 5% aqueous solution of sodium hydrogen carbonate and water. After the organic layer was dried over anhydrous magnesium sulfate, it was filtrated and washed with chloroform. The filtrate and the washing liquid were combined, and a resulting residue was subjected to the flash chromatography (eluent, ethyl acetate: hexane=3:1) to obtain the Compound (5) (556 mg). Yield, 57.6%.

$C_{56}H_{70}NO_{24}FSi$ (1188.25) $[\alpha]_D=+12.3°$ (c 0.64, CHCl$_3$). IR$^{KBr}_{max}$cm$^{-1}$: 3600–3100 (OH, NH), 1730, 1250 (ester), 1670, 1540 (amide), 860, 840 (Me$_3$Si), 710 (phenyl), 500 MHz $^1$H-NMR (CDCl$_3$; TMS): Lactose unit: δ 8.1–7.2 (m, 15H, 3Bz), 5.36 (dd, 1H, $J_{1,2}$=8.1 Hz, $J_{2,3}$=9.5 Hz, H-2), 4.87 (dd, 1H, $J_{gem}$=11.9 Hz, $J_{5,6}$=2.9 Hz, H-6), 4.65 (d, 1H, $J_{1,2}$=8.0 Hz, H-1), 4.56 (d, 1H, $J_{1',2'}$=7.8 Hz, H-1'), 4.62 (dd, 1H, $J_{gem}$=11.9 Hz, $J_{5,6}$=2.9 Hz, H-6), 3.68 (m, 1H, 1H, CHCH$_2$SiMe$_3$), 0.85 (m, 2H, CH$_2$ SiMe$_3$), 0.00 (s, 9H, Me$_3$ Si). Sialic acid unit: δ 5.22 (dd, 1H, $J_{6,7}$=1.7 Hz, $J_{7,8}$=9.3 Hz, H-7), 3.81 (s, 3H, CO$_2$Me), 2.70 (dd, 1H, $J_{3a,3e}$=12.5 Hz, $J_{3e,4}$=5.6 Hz, H-3e) 2.04, 2.08, 2.16 (3s, 9H, 3OAc), 1.90 (s, 3H, NAc). $^{19}$F-NMR (CDCl$_3$; CFCl$_3$): δ -234 (m, 1F, 9-F).

Example 6
Synthesis of 2-(trimethylsilyl)ethyl O-(methyl 5-acetamide-4,7,8-tri-O-acetyl-3,5,9-trideoxy-9-fluoro-D-glycero-α-D-galacto-2-nonulopyrasilonate)-(2→3)-O-(2,4-di-O-acetyl-6-O-benzoyl-β-D-galactopyranosil)-(1→4)-3-O-acetyl-2,6-di-O-benzoyl-β-D-glucopyranoside (Compound (6))

The compound (5) (550 mg, 0.46 mmol) was dissolved in pyridine (30 ml), and acetic anhydride (15 ml) was added to the solution, and stirred overnight at room temperature. Then, the residue obtained by concentration under reduced pressure was subjected to the flash chromatography (eluent, ethyl acetate:

hexane=5:1) to obtain the Compound (6) (461 mg). Yield, 75.7%.

$C_{62}H_{76}NO_{27}FSi$ (1314.36) $[\alpha]_D=+5.18°$ (c 0.89, CHCl$_3$). IR$^{KBr}_{max}$cm$^{-1}$: 3380 (NH), 1750, 1230 (ester), 1690, 1540 (amide), 860, 840 (Me$_3$Si), 710 (phenyl). 500 MHz $^1$H-NMR (CDCl$_3$; TMS): Lactose unit: δ 8.2–7.4 (m, 15H, 3Bz), 5.58 (dd, 1H, $J_{2,3}$=$J_{3,4}$=9.5 Hz, H-3), 5.34 (dd, 1H, H-4'), 5.11 (dd, 1H, $J_{1,2}$=7.9 Hz, $J_{2,3}$=9.5 Hz, H-2), 4.90 (d, 1H, $J_{1',2'}$=8.0 Hz, H-1'), 4.77 (d, 1H, $J_{1,2}$=7.9 Hz, H-1), 4.67 (dd, 1H, $J_{2',3'}$=10.3 Hz, $J_{3',4'}$=3.3 Hz, H-3'), 3.68 (m, 1H, 1H, CHCH$_2$SiMe$_3$), 0.95 (m, 2H, CH$_2$ SiMe$_3$), 0.00 (s, 9H, Me$_3$ Si) Sialic acid unit: δ 5.47 (m, 1H, H-8), 5.32 (dd, 1H, $J_{6,7}$=1.8 Hz, $J_{7,8}$=9.9 Hz, H-7), 3.81 (s, 3H, CO$_2$Me), 2.69 (dd, 1H, $J_{3a,3e}$=12.6 Hz, $J_{3e,4}$=4.6 Hz, H-3e), 2.07, 2.09, 2.11, 2.18, 2.22, 2.30 (6s, 18H, 6OAc), 1.96 (s, 3H, NAc), 1.78 (dd, 1H, $J_{3a,3e}$=$J_{3a,4}$=12.4 Hz, H-3a). $^{19}$F-NMR (CDCl$_3$; CFCl$_3$): δ -234 (dt, 1F, $J_{F,8H}$=25.5 Hz, $J_{F,9H}$=50.5 Hz, 9-F).

Example 7
Synthesis of O-(methyl 5-acetamide-4,7,8-tri-O-acetyl-3,5,9-trideoxy-9-fluoro-D-glycero-α-D-galacto-2-nonulopyrasilonate)-(2→3)-O-(2,4-di-O-acetyl-6-O-benzoyl-β-D-galactopyranosil)-(1→4)-3-O-acetyl-2,6-di-O-benzoyl-β-D-glucopyranoside (Compound (7))

The Compound (6) (456 mg, 0.35 mmol) was dissolved in anhydrous dichloromethane (10 ml). To the solution, boron trifluoride-diethyl ether (0.43 ml, 4.3 mmol) was dropwise added while cooling with ice and stirred at room temperature for 7 hours under argon atmosphere. The mixture was diluted with dichloromethane, and washed with a 5% aqueous solution of sodium hydrogen carbonate and water. The mixture was dried over anhydrous sodium sulfate and filtrated. The filtrate was concentrated under reduced pressure, and the obtained residue was subjected to the flash chromatography (eluent, ethyl acetate hexane=5:1) to obtain the Compound (7) (314 mg). Yield, 74.6%. $C_{57}H_{64}NO_{27}F$ (1214.12) $[\alpha]_D=+31.9°$ (c 1.08, CHCl$_3$). IR$^{KBr}_{max}$cm$^{-1}$: 3600–300 (OH, NH), 1750, 1230 (ester), 1670, 1540 (amide), 715 (phenyl). $^{19}$F-NMR (CDCl$_3$; CFCl$_3$): δ -234 (dt, 1F, $J_{F,8H}$=26.0 Hz, $J_{F,9H}$=50.0 Hz, 9-F).

Example 8
Synthesis of O-(methyl 5-acetamide-4,7,8-tri-O-acetyl-3,5,9-trideoxy-9-fluoro-D-glycero-α-D-galacto-2-nonulopyrasilonate)-(2→3)-O-(2,4-di-O-acetyl-6-O-benzoyl-β-D-galactopyranosil)-(1→4)-3-O-acetyl-2,6-di-O-benzoyl-α-D-glucopyranosil trichloroacetoimidate (Compound (8))

The compound (7) (304 mg, 0.25 mmol) was dissolved in anhydrous dichloromethane (3 ml) under argon atmosphere, and trichloroacetonitrile (0.75 ml, 7.5 mmol) and 1,8-diazabicyclo[5.4.0]-undec-7-ene (0.02 ml, 0.13 mmol) were added to the solution while cooling at −5° C., followed by stirring for 2 hours while cooling with ice. The residue obtained by concentration under reduced pressure was subjected to the flash chromatography (eluent, ethyl acetate:hexane=5:1) to obtain the Compound (8) (206 mg). Yield, 60.6%.

$C_{59}H_{64}N_2O_{27}FCl_3$ (1358.51) $|\alpha|_D$=+37.7° (c 0.52, $CHCl_3$). $IR^{KBr}_{max}cm^{-1}$: 3600–3100 (NH), 1750,1230 (ester), 1680,1540 (amide), 710 (phenyl). 500 MHz $^1$H-NMR ($CDCl_3$; TMS): Lactose unit: δ 8.56 (s, 1H, C=NH), 8.1–7.4 (m, 15H, 3Bz), 6.67 (d, 1H, $J_{1,2}$=3.6 Hz, H-1), 5.85 (dd, 1H, $J_{2,3}$=$J_{3,4}$=8.9 Hz, H-3),5.28 (dd, 1H, $J_{1,2}$=3.6 Hz, $J_{2,3}$=8.9 Hz, H-2), 5.06 (dd, 1H, $J_{1',2'}$=5.8 Hz, $J_{2',3'}$=9.0 Hz, H-2'), 4.88 (br. d, 1H, H-4'), 4.58 (dd, 1H, $J_{2',3'}$=9.0 Hz, $J_{3',4'}$=2.5 Hz, H-3'). Sialic acid unit: δ 5.48 (m, 1H, H-8), 5.43 (m, 1H, H-7), 3.74 (s, 3H, $CO_2Me$), 2.58 (dd, 1H, $J_{3a,3e}$=12.8 Hz, $J_{3e,4}$=4.6 Hz, H-3e), 1.94, 2.00, 2.03, 2.05, 2.12, 2.19 (6s, 18H, 6OAc), 1.84 (s, 3H, NAc),.1.66 (dd, 1H, $J_{3a,3e}$=$J_{3a,4}$=12.4 Hz, H-3a). $^{19}$F-NMR ($CDCl_3$; $CFCl_3$): δ -234 (dt, 1F, $J_{F,8H}$=26.5 Hz, $J_{F,9H}$=49.5 Hz, 9-F).

Example 9
Synthesis of O-(methyl 5-acetamide-4,7,8-tri-O-acetyl-3,5,9-trideoxy-9-fluoro-D-glycero-α-D-galacto-2-nonulopyrasilonate)-(2→3)-O-(2,4-di-O-acetyl-6-O-benzoyl-β-D-galactopyranosil)-(1→4)-(3-O-acetyl-2,6-di-O-benzoyl-β-D-glucopyranosil)-(1→1)-(2S,3R,4E)-2-azido-3-benzoyloxy-4-octadecen-1,3-diol (Compound (9))

The compound (8) (205 mg, 0.15 mmol) and (2S,3R,4E)-2-azido-3-benzoyloxy-4-octadecen-1,3-diol (Compound (B)) (155 mg, 0.36 mmol) were dissolved in dichloromethane (8 ml). To the solution, molecular sieve 4A (3.1 g), which was activated by drying at 180° C. for 6 hours in vacuo, was added and stirred at room temperature for 30 minutes under argon atmosphere. Then, boron trifluoride-diethyl ether (0.43 μl, 0.35 mmol) was dropwise added to the mixture while cooling with ice and stirred at 0° C. for 2.5 hours. The reaction mixture was diluted with dichloromethane, and filtrated through sellaite, and a dichloromethane layer was washed with an aqueous solution of sodium hydrogen carbonate and water, followed by drying over sodium sulfate. The residue obtained by concentration under reduced pressure was subjected to the flash chromatography (eluent, ethyl acetate:hexane=4:1) to obtain the Compound (9) (208 mg). Yield, 84.9%.

$C_{88}H_{101}N_4O_{29}F$ (1625.71) $|\alpha|_D$=−2.6° (c 0.54, $CHCl_3$). $IR_{max}cm^{-1}$: 3650–3180 (NH), 2110 (azide), 1750, 1230 (ester), 1690, 1540 (amide), 710 (phenyl). 500 MHz $^1$H-NMR ($CDCl_3$; TMS): Lactose unit: δ 8.1–7.3 (m, 20H, 4Bz), 5.26 (dd, 1H, $J_{1,2}$=7.8 Hz, $J_{2,3}$=9.6 Hz, H-2), 5.03 (dd, 1H, $J_{1',2'}$=8.0 Hz, $J_{2',3'}$=10.1 Hz, H-2'), 4.99 (br. d, 1H, H-4'), 4.79 (d, 1H, $J_{1',2'}$=8.0 Hz, H-1'), 4.68 (d, 1H, $J_{1,2}$=7.8 Hz,

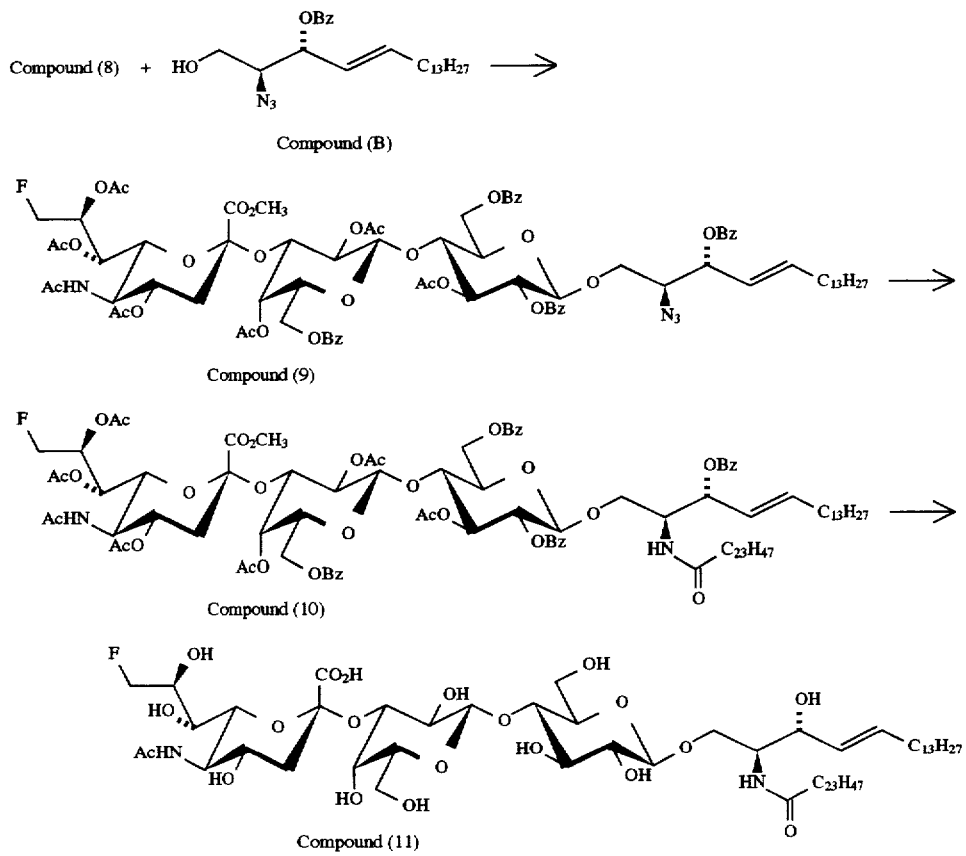

H-1). Sialic acid unit: δ 3.74 (s, 3H, CO₂Me), 3.58 (dd, 1H, J₅,₆=10.9 Hz, J₆,₇=2.0 Hz, H-6), 2.57 (dd, 1H, J₃ₐ,₃ₑ=12.4 Hz, J₃ₑ,₄=4.6 Hz, H-3e), 1.96, 1.99, 2.00, 2.06, 2.11, 2.18 (6s, 18H, 6OAc), 1.85 (s, 3H, NAc),.1.67 (dd, 1H, J₃ₐ,₃ₑ= J₃ₐ,₄=12.4 Hz, H-3a). Sphingosine unit: δ 5.70 (dt, 1H, J₄,₅=14.7 Hz, J₅,₆=J₅,₆=8.2 Hz, H-5), 1.2 (m, 22H, 11CH₂), 0.86 (t, 3H, J=5.7 Hz, CH₃). ₁₉F-NMR (CDCl₃; CFCl₃): δ -234 (dt, 1F, J_{F,8H}=25.5 Hz, J_{F,9H}=50.0 Hz, 9-F).

Example 10
Synthesis of O-(methyl 5-acetamide-4,7,8-tri-O-acetyl-3,5, 9-trideoxy-9-fluoro-D-glycero-α-D-galacto-2-nonulopyrasilonate)-(2→3)-O-(2,4-di-O-acetyl-6-O-benzoyl-β-D-galactopyranosil)-(1→4)-(3-O-acetyl-2,6-di-O-benzoyl-β-D-glucopyranosil)-(1→1)-(2S,3R,4E)-3-benzoyloxy-2-tetracosanamido-4-octadecen-1,3-diol (Compound (10))

The compound (9) (92 mg, 0.06 mmol) was dissolved in a mixed solvent of pyridine and water (=5:1) (12 ml) and stirred at room temperature for 52 hours while blowing hydrogen sulfide therein, followed by solidification under reduced pressure. This residue was dissolved in dichloromethane (4.5 ml), and tetracosanic acid (33 mg, 0.09 mmol) and 1-ethyl-3-(3-dimethyl-aminopropyl) carbodiimide hydrochloride (50 mg, 0.26 mmol) were added to the solution, and stirred overnight at room temperature. The reaction mixture was diluted with dichloromethane and washed with water, followed by drying over anhydrous magnesium sulfate. Then, the mixture was filtrated, and washed with dichloromethane. The filtrate was concentrated under reduced pressure. The obtained residue was subjected to the flash chromatography (eluent, ethyl acetate:hexane= 3:1) to obtain the Compound (10) (52 mg, 47.3%).

$C_{106}H_{149}N_2O_{30}F$ (1950.34) $[\alpha]_D$=+7.13° (c 1.15, CHCl₃). IR$^{KBr}_{max}$cm⁻¹: 3600–3200 (NH), 2920 (methylene, ethylene), 1750, 1230 (ester), 1650, 1540 (amide), 710 (phenyl). 500 MHz 1H-NMR (CDCl₃; TMS):
Lactose unit: δ 8.1–7.3 (m, 20H, 4Bz), 5.19 (dd, 1H, J₁,₂=7.9 Hz, J₂,₃=9.9 Hz, H-2), 5.01 (dd, 1H, J₁',₂=8.0 Hz, J₂',₃'=10.3 Hz, H-2'), 4.75 (d, 1H, J₁',₂=8.0 Hz, H-1'), 4.60 (d, 1H, J₁,₂=7.9 Hz, H-1), 4.55 (dd, 1H, J₂',₃=10.3 Hz, J₃',₄=3.3 Hz, H-3').
Sialic acid unit: δ 3.74 (s, 3H, CO₂Me), 3.63 (dd, 1H, J₅,₆=10.9 Hz, J₆,₇=2.4 Hz, H-6), 2.57 (dd, 1H, J₃ₐ,₃ₑ=12.5 Hz, J₃ₑ,₄=4.6 Hz, H-3e), 1.98, 1.99, 2.00, 2.06, 2.10, 2.16 (6s, 18H, 6OAc), 1.84 (s, 3H, NAc),.1.66 (dd, 1H, J₃ₐ,₃ₑ= J₃ₐ,₄=12.5 Hz, H-3a).
Ceramide unit: δ 5.76 (dt, 1H, J₄,₅=15.3 Hz, J₅,₆=J₅,₆=6.9 Hz, H-5), 5.26 (d, 1H, J_{NH,2}=9.2 Hz, NH), 1.2 (m, 62H, 31CH₂), 0.88 (t, 6H, J=5.7 Hz, 2CH₃). ¹⁹F-NMR (CDCl₃; CFCl₃): δ -234 (dt, 1F, J_{F,8H}=26.0 Hz, J_{F,9H}=51.0 Hz, 9-F).

Example 11
Synthesis of O-(5-acetamide-3,5,9-trideoxy-9-fluoro-D-glycero-α-D-galacto-2-nonulopyrasilonic acid)-(2→3)-O-(β-D-galactopyranosil)-(1→4)-O-(β-D-glucopyranosil)-(1→1)-(2S,3R,4E)-2-tetracosanamido-4-octadecen-1,3-diol (Compound (11))

The compound (10) (48 mg, 0.025 mmol) was dissolved in anhydrous methanol (30 ml), and sodium methoxide (11 mg, 0.20 mmol) was added to the solution and stirred at room temperature for 15 hours. After cooing with ice, water (0.5 ml) was added to the solution, and stirred for 1.5 hours while cooling with ice and further for 2.5 hours at room temperature. After confirming the termination of the reaction by TLC (acetic acid:butanol:water=2:1:1), the reaction mixture was passed through a column containing an ion exchange resin IR-120 (H+) (eluent:methanol), and concentrated under reduced pressure. The residue was gel filtrated through Sephadex LH-20 (eluent:methanol) to obtain the Compound (11) (27 mg). Yield, 86.5%.

$C_{65}H_{119}N_2O_{20}F$ (1267.66) $[\alpha]_D$=+1.32° (c 0.56, CHCl₃ :MeOH=1:1).
IR$^{KBr}_{max}$cm³¹ ⁻¹: 3700–3300 (OH, NH), 2940, 2850 (methyl, methylene), 1720 (ester), 1660, 1540 (amide), 500 MHz ₁H-NMR (CDCl₃-CD₃OD=1:1; TMS):
Lactose unit: δ 4.41 (d, 1H, J₁',₂=7.9 Hz, H-1'), 4.29 (d, 1H, J₁,₂=7.8 Hz, H-1).
Sialic acid unit: δ 2.84 (m, ¹H, H-3e), 2.04 (s, 3H, NAc).
Ceramide unit: δ 5.70 (dt, 1H, J₄,₅=14.9 Hz, J₅,₆=J₅,₆=6.8 Hz 5), 5.45 (dd, 1H, J₃,₄=7.4 Hz, J₄,₅=15.2 Hz, H-4), 1.27 (m, 62H, 31CH₂), 0.89 (t, 6H, J=6.6 Hz, 2CH₃). ¹⁹F-NMR (CDCl₃-CD₃OD=1:1; CFCl₃): δ -234 (dt, 0.9F, J_{F,8H}=26.0 Hz, J_{F,9H}=51.0 Hz, 9-F), -235 (dt, 0.1F, J_{F,8H}=26.0 Hz, J_{F,9H}=51.0 Hz, 9-F).

What is claimed is:

1. A ganglioside GM3 derivative having a fluorine atom at the 9-position of sialic acid represented by the formula:

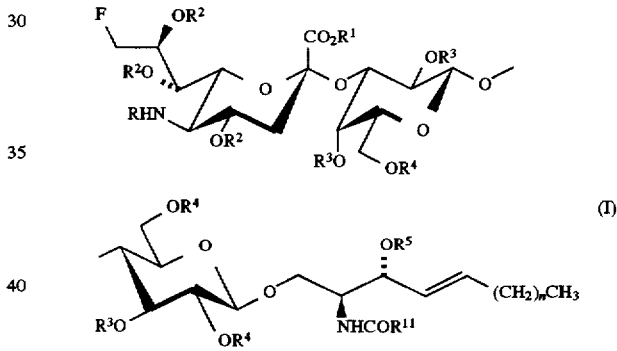

(I)

wherein R is an aliphatic lower acyl group, R¹ is a hydrogen atom or a lower alkyl group, R² to R⁵ represent independently of one another a hydrogen atom, an aliphatic lower acyl group or an aromatic acyl group, R¹¹ is an straight or branched, saturated or unsaturated aliphatic hydrocarbon group having 1 to 30 carbon atoms, and n is an integer of 0 to 20, provided that when R¹ is a hydrogen atom, R² to R⁵ are hydrogen atoms, or when R¹ is a lower alkyl group, R² to R⁵ are each an aliphatic lower acyl group or an aromatic acyl group.

2. A compound of the formula:

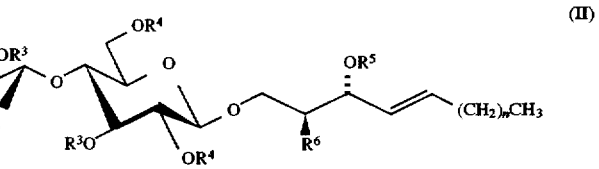

(II)

wherein R is an aliphatic lower acyl group, R¹ is a hydrogen atom or a lower alkyl group, R² to R⁵ represent independently of one another a hydrogen atom, an aliphatic lower acyl group or an aromatic acyl group, n is an integer of 0 to 20, and $R^6$ is a $N_3$ group or a $NH_2$ group, provided that when $R^1$ is a hydrogen atom, $R^2$ to $R^5$ are hydrogen atoms, or when $R^1$ is a lower alkyl group, $R^2$ to $R^5$ are each an aliphatic lower acyl group or an aromatic acyl group.

3. A compound of the formula:

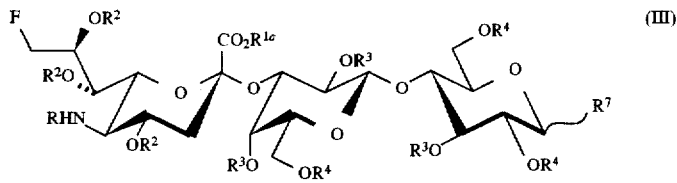
(III)

wherein $R^{1a}$ is a lower alkyl group, $R^7$ is a hydroxyl group, a fluorine atom or a —OC(=NH)CCl$_3$ group, R is an aliphatic lower acyl group, and $R^2$ to $R^4$ represent independently of one another a hydrogen atom, an aliphatic lower acyl group or an aromatic acyl group, provided that when $R^7$ is a fluorine atom or a —OC(=NH)CCl$_3$ group, $R^2$, $R^3$ and $R^4$ are each an aliphatic lower acyl group or an aromatic acyl group.

4. A compound of the formula:

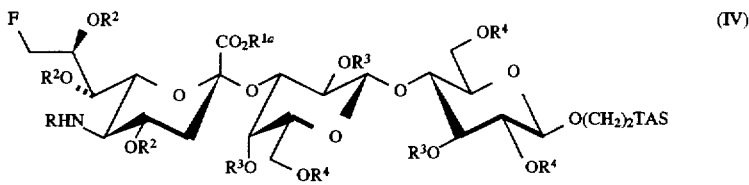
(IV)

wherein TAS represents a trialkylsilyl group, and

R is an aliphatic lower acyl group, $R^{1a}$ is a lower alkyl group, and $R^2$ to $R^4$ represent independently of one another a hydrogen atom, an aliphatic lower acyl group or an aromatic acyl group.

5. A compound of the formula:

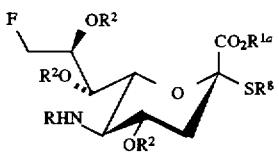
(V)

wherein $R^8$ is a lower alkyl group or an aliphatic acyl group,

R is an aliphatic lower acyl group, $R^{1a}$ is a lower alkyl group, and $R^2$ represents a hydrogen atom, an aliphatic lower acyl group or an aromatic acyl group.

6. A compound of the formula:

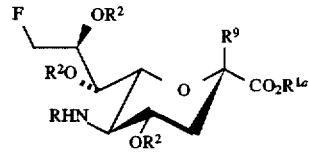
(VI)

wherein $R^9$ is a hydroxyl group or a halogen atom,

R is an aliphatic lower acyl group, $R^{1a}$ is a lower alkyl group, and $R^2$ represents a hydrogen atom, an aliphatic lower acyl group or an aromatic acyl croup.

* * * * *